(12) United States Patent
Chen-Yang et al.

(10) Patent No.: US 8,679,808 B2
(45) Date of Patent: Mar. 25, 2014

(54) METHOD FOR FABRICATING A BIOCOMPOSITE COMPRISING AN AEROGEL WRAPPING A BIOMOLECULE

(75) Inventors: Yui-Whei Chen-Yang, Tao-Yuan (TW); Yen-Kuang Li, Tao-Yuan (TW); Ching-Yao Yuan, Tao-Yuan (TW); Tzong-Yuan Wu, Tao-Yuan (TW)

(73) Assignee: Chung Yuan Christian University, Tao-Yuan (TW)

( * ) Notice: Subject to any disclaimer, the term of this patent is extended or adjusted under 35 U.S.C. 154(b) by 5 days.

(21) Appl. No.: 12/948,124

(22) Filed: Nov. 17, 2010

(65) Prior Publication Data

US 2011/0065820 A1     Mar. 17, 2011

Related U.S. Application Data

(62) Division of application No. 11/938,260, filed on Nov. 10, 2007, now abandoned.

(30) Foreign Application Priority Data

Dec. 28, 2006 (TW) ............................. 95149391 A

(51) Int. Cl.
| | | |
|---|---|---|
| *C12N 11/14* | (2006.01) | |
| *C12N 11/04* | (2006.01) | |
| *G01N 33/551* | (2006.01) | |
| *G01N 33/553* | (2006.01) | |
| *G01N 33/552* | (2006.01) | |
| *G01N 33/549* | (2006.01) | |
| *C07K 17/04* | (2006.01) | |
| *C07K 17/14* | (2006.01) | |

(52) U.S. Cl.
USPC ........... 435/176; 435/182; 436/524; 436/535; 530/811; 530/817

(58) Field of Classification Search
None
See application file for complete search history.

(56) References Cited

U.S. PATENT DOCUMENTS

| | | | | |
|---|---|---|---|---|
| 5,122,291 | A | 6/1992 | Wolff et al. | |
| 7,125,580 | B2 * | 10/2006 | Miller et al. | ................... 427/202 |
| 7,238,729 | B2 * | 7/2007 | Rolison et al. | ................ 521/84.1 |
| 7,618,608 | B1 * | 11/2009 | Keller, Sr. | ...................... 423/338 |
| 7,622,422 | B2 * | 11/2009 | Vioux et al. | ................... 502/405 |
| 7,731,988 | B2 * | 6/2010 | Thomas et al. | ................ 424/423 |

OTHER PUBLICATIONS

Dai et al., Chem. Commun. 2000, 243-244.*

* cited by examiner

*Primary Examiner* — David M Naff
(74) *Attorney, Agent, or Firm* — WPAT, PC; Justin King

(57) ABSTRACT

The present invention discloses a method for fabricating aerogels, a method for fabricating surface-modified aerogels, and a method for fabricating biocomposites. Take the fabricating method of biocomposites for example, first, a precursor solution is provided and the precursor solution comprises a hydrophilic ionic liquid, a catalyzed hydrolysis and/or condensation reagent, at least one biomolecule. Next, a curing process is performed for the precursor solution to hydrolyze and polymerize the at least one alkoxide monomer and/or aryloxide monomer to wrap at least one biomolecule and thus form biocomposite. Afterwards, an extracting process is performed by a solvent for the biocomposite to substitute the ionic liquid in the biocomposite. Finally, a drying process for the biocomposite is carried out after the extracting process so as to remove the solvent in the biocomposite. Therefore, the biocomposite is formed.

22 Claims, 6 Drawing Sheets

(a)

(b)

METHOD FOR FABRICATING A BIOCOMPOSITE COMPRISING AN AEROGEL WRAPPING A BIOMOLECULE

This application is a division of application Ser. No. 11/938,260, filed Nov. 10, 2007, now abandoned.

BACKGROUND OF THE INVENTION

1. Field of the Invention

The present invention is generally related to a method for fabricating aerogels, and more particularly to a method utilizing an ionic liquid for fabricating aerogels and their applications in biocomposites.

2. Description of the Prior Art

Aerogel is very light weighted. Aerogel is also called "frozen smoke", because its density can be as low as 0.003 g/cm$^3$. It is a species of solid with very slim skeleton because its porosity can be as high as 99.9%. The solid is filled with air and thus called "aerogel". It has a pore network structure and very high specific surface area to hold 1600 times its weight. However, the only drawback is that its structure is very brittle.

Almost all of the applications of aerogel are related to the network structure with porosity higher than 90%. Aerogel has the characteristics of low density, low heat conductivity, low sound spreading speed, low dielectric constant and so forth to become excellent heat-insulating, sound-insulating, electrical insulating materials. It can be used in heat-insulating material, sound-insulating material, electrical insulating material, adsorption material, catalyst, catalyst support, filtering material, dust collecting material, detectors, and capacitors, etc. It can be applied in very broad areas. In addition, it can be applied in the areas of medicine and pesticide as the drug controlled release carrier.

Generally, metal oxide aerogel catalyst is fabricated by using metal alkoxides as a precursor, using sol-gel technique to synthesize wet gel, and then carrying out supercritical fluid extraction and drying. However, the temperature and pressure conditions for supercritical fluid are very harsh. Under such conditions, the activity of the enclosed biomolecule may be destroyed or the enclosed target drug may be extracted and removed. These conditions are not suitable for fabricating biocomposite or bio-wrapping materials. Besides, the procedures for supercritical fluid treatment are very complicated and minute and the operating process may cause explosion. Therefore, a novel method for fabricating aerogel is required to meet the requirements of the industry.

SUMMARY OF THE INVENTION

In light of the above background, the present invention provides a new method for fabricating aerogels and their applications in biocomposites.

One object of the present invention is to use ionic liquids with different properties and to control their added amount so as to adjust the pore diameter and specific surface area of aerogel. Since the ionic liquid has the characteristics of non-volatility, non-ignitibility, easy preparation, easy separation, and easy recycling, it can replace organic solvents and traditional supercritical fluid processes to thereby satisfy the trend of environmental protection.

Another object of the present invention is to provide a method for fabricating surface modified aerogel. It can be applied in preparation of organic/inorganic composites and bio-aerogel composites to be used as adsorbing, catalyzing, separating, drug release materials. Therefore, the present invention does have the economic advantages for industrial applications.

Accordingly, the present invention discloses a method for fabricating aerogel, a method for fabricating surface-modified aerogel, and a method for fabricating biocomposite. Take the fabricating method of biocomposites for example, first, a precursor solution is provided and the precursor solution comprises a hydrophilic ionic liquid, a catalyzed hydrolysis and/or condensation reagent, at least one biomolecule.— Next, a curing process is performed for the precursor solution to hydrolyze and polymerize the at least one alkoxide monomer and/or aryloxide monomer to wrap at least one biomolecule and thus form biocomposite. Afterwards, an extracting process is performed by a solvent for the biocomposite to substitute the ionic liquid in the biocomposite. Finally, a drying process for the biocomposite is carried out after the extracting process so as to remove the solvent in the biocomposite. Therefore, the biocomposite is formed.

DESCRIPTION OF THE PREFERRED EMBODIMENTS

Figure 1:
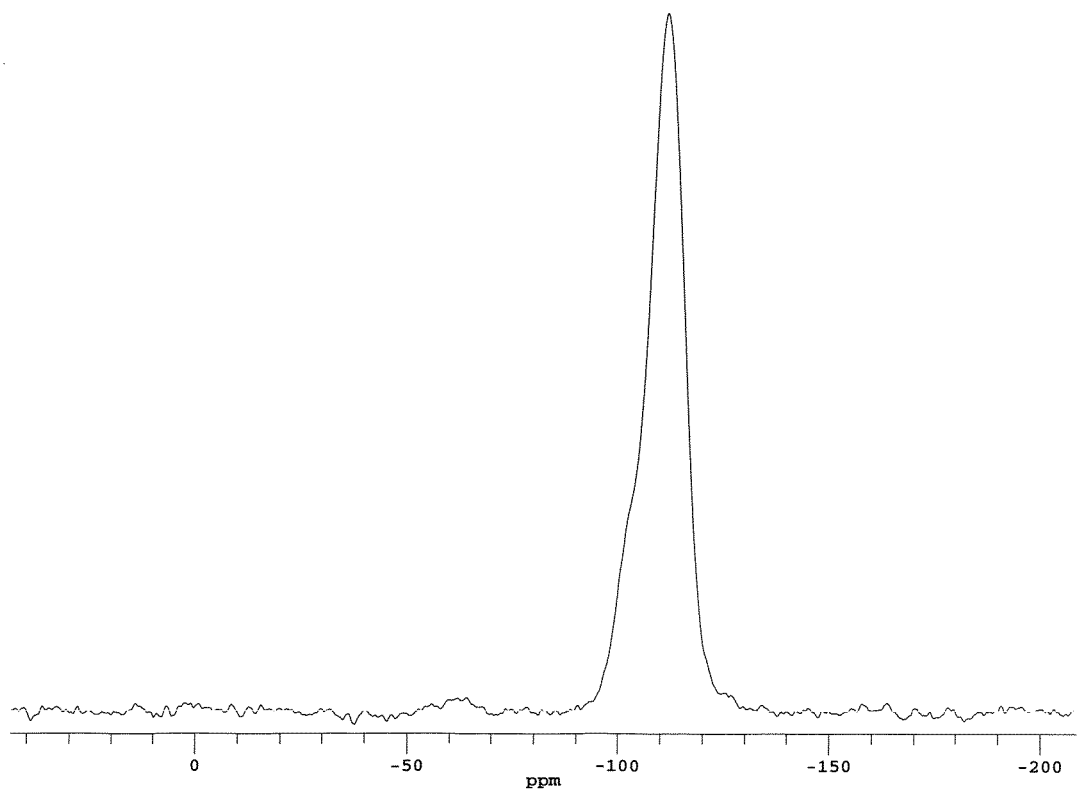
FIG. 1 shows the result of the solid state $^{29}$Si-NMR spectrum of the silica aerogel according to the first embodiment of the present invention.

What is probed into the invention is a method for fabricating aerogels and their applications in biocomposites. Detail descriptions of the structure and elements will be provided in the following in order to make the invention thoroughly understood. Obviously, the application of the invention is not confined to specific details familiar to those who are skilled in the art. On the other hand, the common structures and elements that are known to everyone are not described in details to avoid unnecessary limits of the invention. Some preferred embodiments of the present invention will now be described in greater detail in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In a first embodiment of the present invention, a method for fabricating an aerogel is provided. At first, a precursor solution is provided and the precursor solution comprises an ionic liquid, a catalyzed hydrolysis and/or condensation reagent, and at least one alkoxide monomer and/or aryloxide monomer. The ionic liquid is used as a template as well as a solvent.

The central element of the alkoxide monomer and/or aryloxide monomer comprises one selected from the group consisting of the following: Li, Na, K, Rb, Cs, Be, Mg, Ca, Sr, Ba, Ti, Te, Cr, Cu, Er, Fe, Ta, V, Zn, Zr, Al, Si, Ge, Sn, and Pb. The common alkoxide monomer and/or aryloxide monomer comprises one selected from the group consisting of the following: tetramethyl orthosilicate (TMOS), tetraethoxy orthosilicate (TEOS), bis(triethoxysilyl)ethane (BTSE), bis (triethoxysilyl)benzene (BTSB), tetrabutyl titanate (TBOT), and vanadium oxytriproposide. The catalyzed hydrolysis and/or condensation reagent comprises one selected from the group consisting of the following or any combination of the following: alcohol (the number of carbon is less than or equal to 5), acidic compound, and alkaline compound. Thus, the reagent catalyzes the hydrolysis and condensation of the alkoxide monomer and/or aryloxide monomer. Besides, another method for forming the precursor solution comprises blending the alkoxide monomer and/or aryloxide monomer with the ionic liquid to form a first mixture. Next, an acidic compound is added to the first mixture to form a second mixture. Finally, an alkaline compound is added to the second mixture to enhance the hydrolysis and condensation of the alkoxide monomer and/or aryloxide monomer.

Following that, a blending process for the precursor solution is carried out, such as vigorous stir or shake, to disperse each composition in the precursor solution, especially the ionic liquid. Since the ionic liquid is also used as a template, adequate dispersion of templates can increase the pore volume of the obtained aerogel and have the alkoxide monomer and/or aryloxide monomer fully hydrolyzed and polymerized. The blending process continues until the viscosity of the precursor solution reaches a specific viscosity that is more than or equal to 150 cps. A preferred viscosity is more than or equal to 200 cps. After the blending process is complete, the precursor solution is setting to have the alkoxide monomer and/or aryloxide monomer continue to undergo hydrolysis and condensation so as to form the aerogel.

The blending process promotes the porosity and mechanical property of the final aerogel product. In the example of silica aerogel, as shown in FIG. 1, the final sample is grinded and then analyzed by a solid state $^{29}$Si-NMR spectrometer. The relative position and structure of silicide in solid state $^{29}$Si-NMR are shown in Table 1. As shown in FIG. 1, two absorption peaks are observed, at $\delta=-102$ and $-107\sim-110$ ppm, in which the major absorption peak at $\delta=107\sim-110$ ppm is related to a structure $Q^4$ and its intensity is much more than that at $\delta=-102$ ppm, related to a structure $Q^3$. As the alkoxide monomer is TEOS, $Q^2$, $Q^3$, and $Q^4$ are formed according to the hydrolyzing degree. $Q^2$ and $Q^3$ transform into $Q^4$, if $Q^2$ and $Q^3$ are condensed. In addition, the intensities of the peaks for $Q^2$ and $Q^3$ are relatively decreased while that for $Q^4$ is increased. Therefore, the more the $Q^4$ structures are, the more the siloxane hydrolysis is complete and the better the degree of crosslinking is, as shown in FIG. 1.

TABLE 1

| Structure | HO—Si(OR)(OR)—OH | HO—Si(OR)(OR)—OR | RO—Si(OR)(OR)—OR |
|---|---|---|---|
| Peak | $Q^2$ | $Q^3$ | $Q^4$ |
| $\delta$ (ppm) | −91 | −101 | −109 |

As the catalyzed hydrolysis and/or condensation reagent comprises alcohol, the blending process can comprise a heating process. The temperature of the heating process ranges from a room temperature to 70° C. The common composition of the aerogel comprises one selected from the group consisting of the following or any combination of the following: $SiO_2$, $TiO_2$, $V_2O_5$, and $Al_2O_3$. The average pore diameter of the aerogel ranges about 1 nm to 50 nm. The porosity is 50%~99%. The pore volume is more than or equal to 1.0 cm$^3$/g. Besides, the specific surface area depends on the type of aerogel. For example, the specific surface area of $SiO_2$ aerogel is more than or equal to 500 m$^2$/g, that of $V_2O_5$ aerogel is more than or equal to 100 m$^2$/g, and that of $TiO_2$ or $Al_2O_3$ aerogel is more than or equal to 200 m$^2$/g.

Furthermore, after aerogel are formed, an extracting process by a solvent for the aerogel is carried out to substitute the ionic liquid in the pores of the aerogel. Then, a drying process is carried out to remove the solvent in the pores of the aerogel. A preferred solvent for the extracting process is a low boiling point solvent, whose boiling point is less than or equal to 200° C. The solvent comprises one selected from the group consisting of the following: nitrile, alcohol, ketone, and water. The temperature of the extracting process ranges from 50° C. to 200° C. Since the method for fabricating aerogel according to this embodiment comprises the blending process, hydrolysis is more complete and the aerogel product with high crosslinking network structures can be formed. Even though water having high interfacial tension is used as the extraction solvent during the extracting process, it dose not cause the pore structure of aerogel to crash. Aerogel can have high porosity and network structure.

In this embodiment, the ionic liquid is a room temperature ionic liquid and is formed by mixing an organic base with a Lewis acid. When the Lewis acid is halogenated metal acid, it can form a room temperature ionic liquid but will produce halogen acid if reacting with water. Therefore, the halogenated metal acid is not suitable for the present invention. The Lewis acid used by the present invention is not halogenated metal acid so as to prepare a stable ionic liquid in water. In a preferred example, the cationic moiety in the organic base has the following general equation:

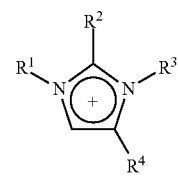

in which $R^1$, $R^2$, $R^3$, and $R^4$ are selected according to the following table.

| $R^1$ | $R^2$ | $R^3$ | $R^4$ |
|---|---|---|---|
| $CH_3$ | H | $CH_3$ | H |
| $C_2H_5$ | H | $CH_3$ | H |
| $C_2H_5$ | H | $C_2H_5$ | H |
| $CH_3CH_2CH_2CH_2$ | H | $CH_3$ | H |
| $(CH_3)_2CHCH_2$ | H | $CH_3$ | H |
| $CH_3CH_2CH_2CH_2$ | H | $C_2H_5$ | H |
| $CH_3$ | H | $CH_3OCH_2CH_2$ | H |
| $CH_3$ | H | $CF_3CH_2$ | H |
| $CH_3$ | $CH_3$ | $C_2H_5$ | H |
| $CH_3$ | $CH_3$ | $CH_3CH_2CH_2$ | H |
| $C_6H_6CH_2$ | $CH_3$ | $CH_3CH_2CH_2$ | H |
| $C_6H_6CH_2$ | $CH_3$ | $CH_3CH_2CH_2CH_2$ | H |
| $C_6H_6CH_2$ | $CH_3$ | $(CH_3CH_2)(CH_3)CH$ | H |

-continued

| R$^1$ | R$^2$ | R$^3$ | R$^4$ |
|---|---|---|---|
| C$_6$H$_6$CH$_2$ | CH$_3$ | CH$_3$CH$_2$CH$_2$CH$_2$ | H |
| CH$_3$ | H | C$_2$H$_5$ | CH$_3$ |
| C$_2$H$_5$ | H | C$_2$H$_5$ | CH$_3$ |

For example, the common cation of the organic base comprises one selected from the group consisting of the following: 1-n-butyl-3-methylimidazolium (BMI), 1-octanyl-3-methylimidazolium (OMI), 1-dodecanyl-3-methylimidazolium (DMI), and 1-hexadecanyl-3-methylimidazolium (HDMI). In addition, the anionic moiety in the Lewis acid comprises one selected from the group consisting of the following: BF$_4^-$, PF$_6^-$, AsF$_6^-$, SbF$_6^-$, F(HF)$_n^-$, CF$_3$SO$_3^-$, CF$_3$CF$_2$CF$_2$CF$_2$SO$_3^-$, (CF$_3$SO$_2$)$_2$N$^-$, (CF$_3$SO$_2$)$_3$C$^-$, CF$_3$COO$^-$, and CF$_3$CF$_2$CF$_2$COO$^-$. When the organic base to be used is determined, the anionic moiety in the Lewis acid can be adjusted to control hydrophilicity/hydrophobicity of the ionic liquid. For example, BMI-BF$_4$ is hydrophilic and BMI-(TFSI)$_2$ is hydrophobic.

For instance, silanoxide monomer is used as an example. Silanoxide monomer is hydrolyzed to form hydrophilic silanol (—Si—O—H). Thus, the hydrophilic ionic liquid and silanol are tended to attract to each other and can stabilize the formation of silica structure so as to obtain more stable silica aerogel. Because the hydrophobic ionic liquid repels water and also repels silanol in sol as well as silicon-hydrogen-oxygen group on the surface of silica, the hydrophobic ionic liquid and the silicon-hydrogen-oxygen group do not attract to each other so that the silica structure reaches unstable. Therefore, the silica aerogel fabricated by the hydrophilic ionic liquid has a larger aggregated particle radius and a smaller pore diameter.

In this embodiment, the weight of the ionic liquid is about 10%~90% weight of the at least alkoxide monomer and/or aryloxide monomer and preferably about 20%~50%.

In this embodiment, when the central element of the alkoxide monomer and/or the aryloxide monomer is the same, the specific surface area of aerogel increases with the increase of the molecular weight of the non-alkoxyl block in the alkoxide monomer. For example, in the case of alkoxide monomer and/or aryloxide monomer, when tetramethyl orthosilicate (TMOS), tetraethoxy orthosilicate (TEOS), bis(triethoxysilyl)ethane (BTSE), and bis(triethoxysilyl)benzene (BTSB) are separately used as the precursor, it is found that the specific surface area of the aerogel by using BTSE or BTSB is greater than that by using TMOS or TEOS. It is speculated that the increase of the quantities of pores in the aerogel as well as the increase of the specific surface area are because the vinyl group of BTSE and the phenyl group of the BTSB occupy the networking space in the aerogel.

The method for fabricating aerogel according to this embodiment can be applied in the preparation of TiO$_2$ series aerogel. Semiconductor material has been developed for a period of time. In photo-catalyzed reactions, the characteristic of transforming solar energy to chemical energy is especially worth studying. For example, semiconductor materials, such as TiO$_2$, ZnS, and SnO$_2$, can be utilized as photocatalyst. TiO$_2$ is the most common one used in photo-catalyzed reactions.

Generally, the activity of catalyst is increased with the increase of its specific surface area. However, the specific surface area and the pore volume of TiO$_2$ prepared by the traditional sol-gel method are both small. Although the specific surface area and the pore volume of TiO$_2$ aerogel prepared by supercritical carbon dioxide technique are larger, the processes for such supercritical fluid are very complicated and minute as well as dangerous. Therefore, the ionic liquid without vapor pressure and having a high boiling point replaces supercritical carbon dioxide to be used as a solvent in this embodiment to prepare TiO$_2$ aerogel with larger specific surface area and larger pore volume. On the other hand, compared to SiO$_2$ aerogel, the network structure of TiO$_2$ aerogel are easy to be compressed so that the specific surface area and the activity are relatively low. Therefore, the ionic liquid in this embodiment is used as a template as well as a solvent. Silicon alkoxide monomer and/or aryloxide monomer, such as tetramethyl orthosilicate (TMOS), tetraethoxy orthosilicate (TEOS), bis(triethoxysilyl)ethane (BTSE), and bis(triethoxysilyl)benzene (BTSB), is copolymerized with titanium alkoxide monomer and/or aryloxide monomer, such as tetrabutyl titanate (TBOT) to prepare SiO$_2$—TiO$_2$ two-component aerogel so as to improve the weak point of TiO$_2$ aerogel. Thereby, the application of TiO$_2$ aerogel in catalyst is promoted. The molar ratio of the monomer for silicon source to that for titanium source ranges from 1:9 to 5:5.

In a second embodiment of the present invention, a method for fabricating surface modified aerogel is provided. At first, an precursor solution is provided and the precursor solution comprises at least one alkoxide monomer and/or aryloxide monomer, a catalyzed hydrolysis and/or condensation reagent, an ionic liquid, and an alkoxide monomer and/or aryloxide monomer with at least one specific moiety. The ionic liquid is used as a template as well as a solvent. The specific moiety comprises one selected from the group consisting of the following: carboxyl group, mercapto group, amino group, diamino group, alkyl group (such as methyl group), aryl group (such as phenyl group), epoxy group, and cyano group. The catalyzed hydrolysis and/or condensation reagent comprises one selected from the group consisting of the following or any combination of the following: alcohol (the number of carbon is less than or equal to 5), acidic compound, and alkaline compound. Thus, the reagent catalyzes the hydrolysis and condensation of the alkoxide monomer and/or aryloxide monomer and the alkoxide monomer and/or aryloxide monomer with at least one specific moiety. Besides, another method for forming the precursor solution comprises blending the alkoxide monomer and/or aryloxide monomer, the ionic liquid, and the alkoxide monomer and/or aryloxide monomer with at least one specific moiety to form a first mixture. Next, an acidic compound is added to the first mixture to form a second mixture. Finally, an alkaline compound is added to the second mixture to enhance the hydrolysis and condensation of the alkoxide monomer and/or aryloxide monomer and the alkoxide monomer and/or aryloxide monomer with at least one specific moiety.

Following that, a curing process for the precursor solution is carried out to hydrolyze and polymerize the alkoxide monomer and/or aryloxide monomer and the alkoxide monomer and/or aryloxide monomer with at least one specific moiety so as to form aerogel. The curing process comprises a blending process and a setting process. At first, a blending process for the precursor solution is carried out, such as vigorous stir or shake, to disperse each composition in the precursor solution, especially the catalyzed hydrolysis and/or condensation reagent so as to have the alkoxide monomer and/or aryloxide monomer fully hydrolyzed and polymerized. The blending process continues until the viscosity of the precursor solution reaches a specific viscosity that is more than or equal to 150 cps. A preferred viscosity is more than or equal to 200 cps. After the blending process is complete, the precursor solution is setting to have the alkoxide monomer and/or aryloxide monomer continue to undergo hydrolysis and condensation so as to form the aerogel.

As the catalyzed hydrolysis and/or condensation reagent comprises alcohol, the blending process can comprise a heating process. The temperature of the heating process ranges from 50° C. to 150° C. The common composition of the aerogel comprises one selected from the group consisting of the following or any combination: $SiO_2$, $TiO_2$, $V_2O_5$, and $Al_2O_3$. The average pore diameter of the aerogel ranges about 1 nm to 50 nm. The specific surface area is more than or equal to 100 $m^2$/g. The porosity is 50%~99%.

Furthermore, after the curing process, an extracting process by a solvent for the aerogel is carried out to substitute the ionic liquid in pores of the aerogel. Then, a drying process is carried out to remove the solvent in the pores of the aerogel. A preferred solvent for the extracting process is a low boiling point solvent, whose boiling point is less than or equal to 200° C. The solvent comprises one selected from the group consisting of the following: nitrile, alcohol, ketone, and water. The temperature of the extracting process ranges from 50° C. to 200° C.

In this embodiment, the selection of the central element of the alkoxide monomer and/or aryloxide monomer, the selection of the acidic compound, the temperature range for hydrolyzing and dehydration-polymerizing reactions, and the type and the amount of the ionic liquid are in the same manner as those in the first embodiment. In addition, the alkoxide monomer and/or aryloxide monomer with at least one specific moiety comprises one selected from the group consisting of the following: 3-Aminopropyltriethoxysilane, N-(2-Aminoethyl)-3-amino-propyltriethoxysilane (TMsen), 2-Cyanoethyltriethoxysilane (CNTS), Epoxypropoxypropyltriethoxysilane (EPTS), Methyltriethoxysilane (METS), and Phenyltriethoxysilane (PHTS).

Why do the surfaces of aerogel need to be modified? In the example of silica aerogel, any type of silicon-hydrogen-oxygen group on the surface of amorphous silicon dioxide is called "hydroxylation surface". The hydroxylation surface absorbs water due to hydrogen bonding, while exposing in a hydrous environment. Since pure silica aerogel has unique pore property, specific surface area, and hardness, the chemical and physical characteristics after surface modification treatment can have unique applications. For instance, the application in analysis can be used in (a) column fillers; and (b) adsorption and separation of metallic ions. In catalyst, it can (a) directly catalyze surface functional groups; (b) catalyze surface metal complexes; and (c) be used in composites. In bio-related applications, it can be applied in (a) biosensors and (b) biochips.

Indeed, the method for fabricating aerogel according to this embodiment can be applied in the preparation of surface-modified $TiO_2$ aerogel. On the other hand, the aerogel prepared by the method for fabricating surface-modified aerogel according to this embodiment can be utilized in the preparation of composite polymer electrolytes (CPEs) and can be blended with polymers to fabricate high-tech textiles and bio-composites.

In this embodiment, the alkoxide monomer and/or aryloxide monomer with at least one specific moiety weights about 20%~50% of the weight of the at least one alkoxide monomer and/or aryloxide monomer. Besides, in the example of silanes, as the specific moiety is amino group or diamino group, the specific surface area and the pore diameter of the surface-modified aerogel decreases with the increase of the content of amino and diamino silanes. On the other hand, when the surface-modified aerogel is tested for metallic ion adsorption, it is found that the surface-modified aerogel can adsorb Cu(II) and Zn(II).

Similar to that in the first embodiment, when the central element of the alkoxide monomer and/or the aryloxide monomer is the same, the specific surface area of aerogel increases with the increase of the molecular weight of the non-alkoxyl block in the alkoxide monomer and/or the aryloxide monomer. Therefore, the present invention uses the alkoxide monomer and/or the aryloxide monomer having a plurality of central elements to increase the specific surface area of aerogel so as to enhance the adsorption and catalysis effects.

When the specific moiety on the metal alkoxide is alkyl group (such as methyl group) or aryl group (such as phenyl group), the specific surface area of the surface-modified aerogel changes with the content of alkyl or aryl silane. On the other hand, when the surface-modified aerogel is placed in aqueous solution, it is found that the aerogel cannot be drowned so as to prove that the surface property of the aerogel is converted from hydrophilic to hydrophobic.

When the specific moiety on the metal alkoxide can react with hydroxyl group, such as epoxy group, the specific surface area of the surface-modified aerogel changes with the content of the specific moiety.

In the embodiment of the present invention, the pore diameter and the specific surface area of the aerogel are adjusted by using different types of ionic liquids and controlling its added amount. On the other hand, the method for fabricating aerogel according to this embodiment can be applied in adsorption, catalysis, organic/inorganic composite, and bio-aerogel composite. Therefore, the present invention does have the economic advantages for industrial applications.

In a third embodiment of the present invention, a method for fabricating biocomposite is disclosed. Biocomposite can be applied in variety of fields, such as immobilized enzyme, drug controlled release, bio-separation technique, and sensors, etc.

The definition of "immobilized enzyme" is that enzyme is confined in a specific region but its active site is not hindered so that enzyme can be repeatedly used and continuously operated to thereby reduce the usage of the enzyme and to be effectively separated from the final product. There are numerous methods to immobilize enzyme, generally such as adsorption method, ionic bonding method, covalent bonding method, crosslinking method, and embedding method. Among these, since the covalent bonding method, fixing enzyme on a support, has the advantages of intense bonding force and high stability, it is the most common method for immobilizing enzyme. The immobilized enzyme has many advantages, such as being reusable, being quickly separated from the product, and having increased stability of enzyme.

Drug controlled release technique flourishing from 1970s primarily uses various physical, chemical, and biological methods to control the drug concentration in the blood through delivery system so as to control the drug concentration in the receiving location and to thereby achieve different corresponding pharmacological effect. On the research about drug controlled release, the majority are about development of new material and the change of material property. Among these, the most common method is to control drug release speed by the osmosis of polymer materials. In the past, the characteristic of imbibition of polymer hydrocolloid is used to control the release speed. The delivery mechanism for drugs in polymer membrane is also a common topic.

In bio-molecule recognition, the so-called molecular template technique uses the characteristic of complementary shapes to carry out separation. Different bio-molecules have different specific shapes, like a key with a special shape. Thus, separating a specific molecule from various molecules requires a correct lock. In other words, fabricating a special material for selecting a specific molecule requires obtaining a target molecule as the template, using the target molecule and an effective monomer to form a complex compound, and then using a crosslinking agent to have condensation reaction. After removing the template (target molecule), the shape of the molecule is formed in the structure of the polymer. Finally, the polymer has the functionality of recognizing the molecule. The material fabricated by the molecular template technique usually has very high recognition capability for special molecules and thus can be used to detect or separate micro bio-molecules, such as proteins, saccharides, viruses, and microbes, etc. It can be extensively applied in detection of diseases or food. The molecular template technique together with electronic technique can be used to design membrane sensors for detecting different molecules and for further analysis from the detected output signal. Moreover, the molecular template technique can be applied in simulating the combination reaction of antigen antibody or enzyme substrate, providing catalysis to promote chemical reaction, developing various biological research or analyzing tools for medical detection, and so forth.

This embodiment discloses a method for fabricating biocomposite. At first, a precursor solution is provided and the precursor solution comprises a hydrophilic ionic liquid, a catalyzed hydrolysis and/or condensation reagent, and at least one alkoxide monomer and/or aryloxide monomer. The catalyzed hydrolysis and/or condensation reagent comprises one selected from the group consisting of the following or any combination of the following: alcohol and buffer for biomolecules. The pH value of the buffer is 5~9. Then, a curing process for the precursor solution is carried out to hydrolyze and polymerize the at least one alkoxide monomer and/or aryloxide monomer to wrap at least one biomolecule and thus form biocomposite. An extracting process by a solvent for the biocomposite is carried out to substitute the ionic liquid in the biocomposite. Next, a drying process for the biocomposite is carried out after the extracting process so as to remove the solvent in the biocomposite.

When the biocomposite is applied in separation, there are two common forms. In a first form, the biocomposite is cracked to form a plurality of biocomposite. Then, the biocomposite are filled in a separation column so as to form a bio-separation device. In a second form, the biocomposite is directly formed on the inner surface of a column, such as capillary column so as to form another type of bio-separation device.

The biomolecule comprises one selected from the group consisting of the following: antigens, monoclonal antibodies, polyclonal antibodies, nucleic acids including monomeric and oligomeric types, proteins, enzymes, lipids, polysaccharides, sugars, peptides, polypeptides, drugs, viruses, microbes, and bioligands.

The hydrophilic ionic liquid is a room temperature ionic liquid. A preferred one is selected form those in the first embodiment, such as $BMIC-BF_4$, so as to be mixed with hydrophilic micromolecules. The selection of the alkoxide monomer and/or aryloxide monomer and its central element and the weight range of the hydrophilic ionic liquid are in the same manner as those in the first embodiment. The average pore diameter of the biocomposite ranges about 1 nm to 50 nm. The specific surface area is more than or equal to 100 $m^2/g$. The porosity is 50%~99%. The pore volume is more than or equal to 1.0 $cm^3/g$.

In this embodiment, the curing process comprises a blending process and a setting process. At first, a blending process for the precursor solution is carried out, such as vigorous stir or shake, to disperse each composition in the precursor solution, especially the template-ionic liquid so as to have the alkoxide monomer and/or aryloxide monomer fully hydrolyzed and polymerized. The blending process continues until the viscosity of the precursor solution reaches a specific viscosity that is more than or equal to 150 cps. A preferred viscosity is more than or equal to 200 cps. After the blending process is complete, the precursor solution is setting to have the alkoxide monomer and/or aryloxide monomer continue to undergo hydrolysis and condensation so as to form the biocomposite.

The biocomposite fabricated by this embodiment has the functionality of molecular template and besides can maintain the activity of the biomolecule. By affinity between the same biomolecules, a better result in separation can be achieved. In order to maintain the activity of the biomolecule, the parameters for the process and the operating range are very important. For example, the temperature of the curing process is less than or equal to 50° C. The solvent for the extracting process comprises one selected from the group consisting of the following or any combination of the following: alcohol, water, and buffer solution for biomolecules. The pH value of the buffer solution is 5~9. The temperature of the extracting process is less than or equal to 50° C. The drying process is a freeze-drying process. Its pressure is less than or equal to 20 Pa. The selection of the temperature of the freeze-drying process depends on the extraction solvent. When the extraction solvent is water, the temperature of the drying process is less than or equal to 0° C. When the extraction solvent is alcohol, the temperature of the drying process is less than or equal to −20° C.

Figure 2:
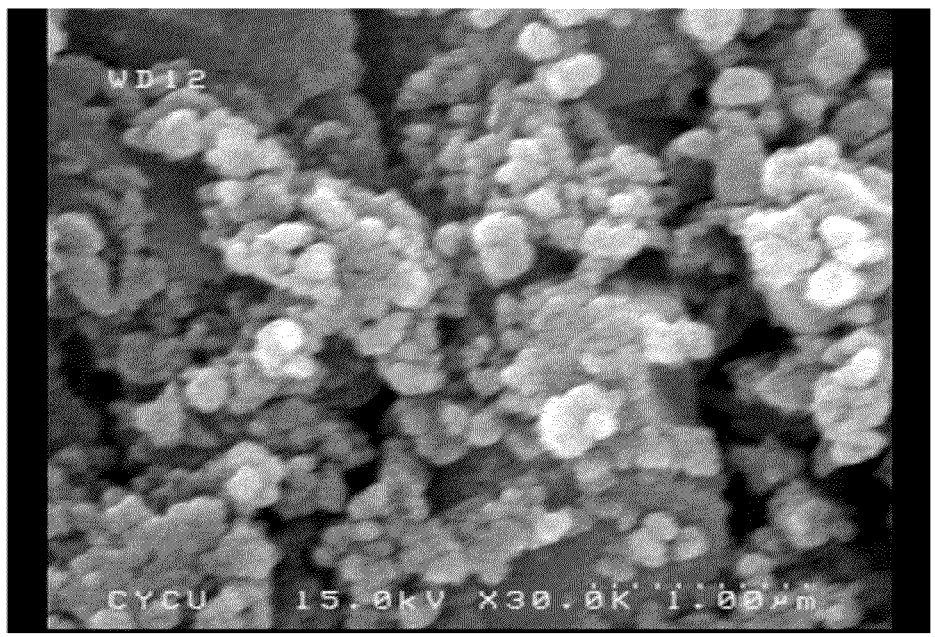
FIG. 2 shows the scanning electron microscopic (SEM) images of the biowrapping material according to the third embodiment of the present invention where (a) magnification is 30 k and (b) 300 k.
Figure 2:
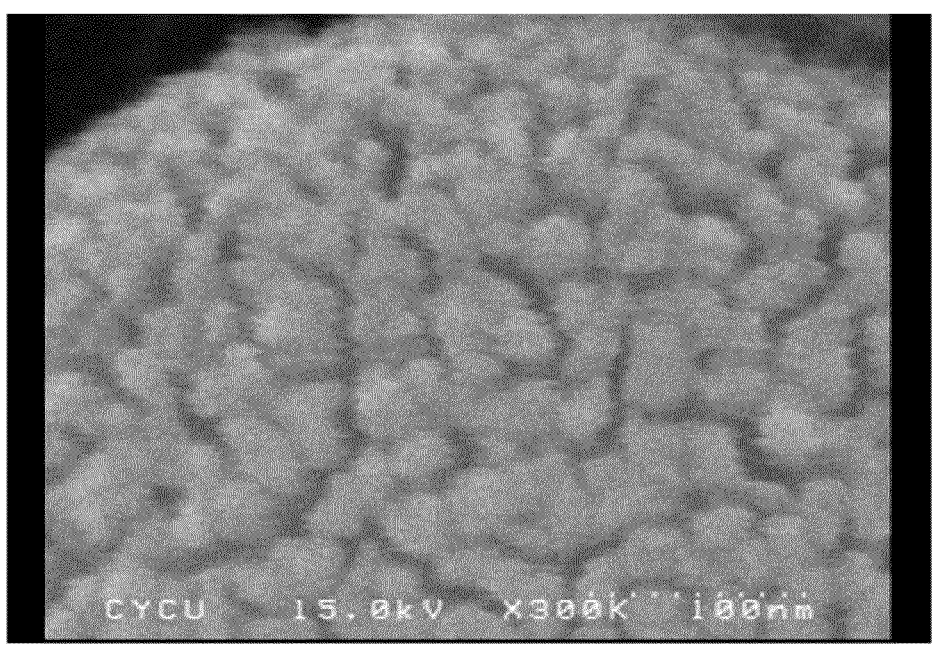

For example, Discosoma red fluorescent protein (DsRed) is used as the template and silica aerogel is used as the substrate. The test result of the fabricated bio-wrapping material is as follows:

1. Test by a Scanning Electron Microscope (SEM):

As shown in FIG. 2, SEM is used to observe the microscopic feature of the aerogel surface. FIG. 2(*a*) has magnification of 30 k and the spherical feature of the silica aerogel surface is seen. FIG. 2(*b*) has magnification of 300 k and it is observed that the spherical feature is comprised of a plurality of smaller silica. Each silica is about a size of 20~30 nm. Therefore, the substrate is a nano-scale aerogel porous material.

Figure 3:
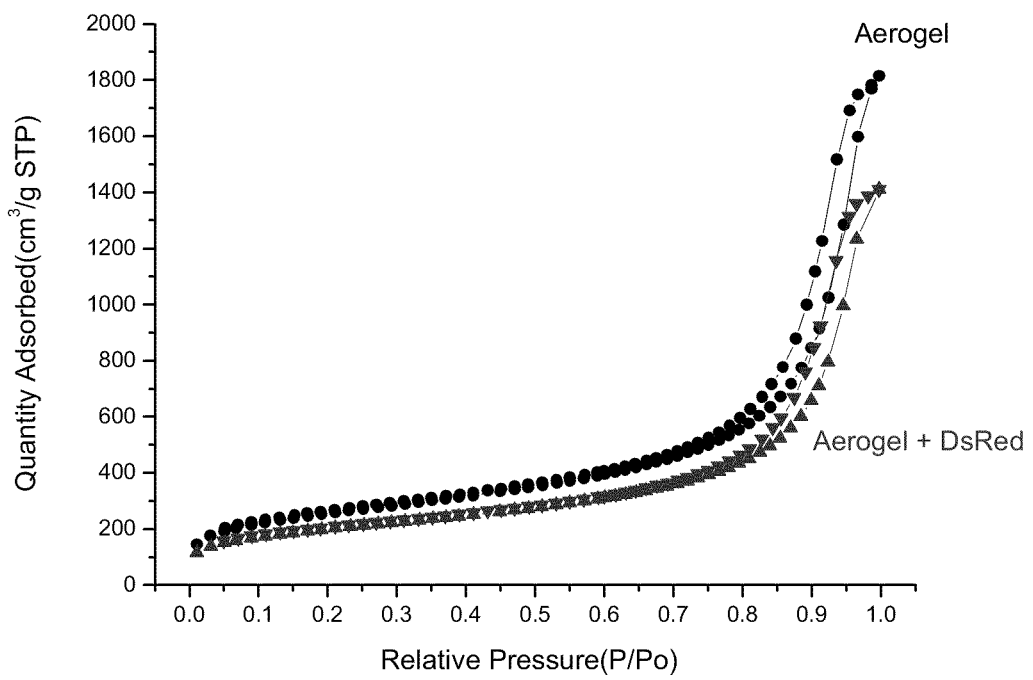
FIG. 3 shows nitrogen adsorption-desorption curves of silica aerogel, silica aerogel wrapping DsRed (Aerogel+DsRed)

2. Nitrogen Adsorption-Desorption Test:

FIG. 3 shows the nitrogen adsorption-desorption curves of silica aerogel, silica aerogel wrapping DsRed (Aerogel+DsRed). The prepared silica aerogel has specific surface area of about 768 $m^2/g$, pore volume of 2.1 $cm^3/g$, and an average pore diameter of 14.0 nm. After wrapping DsRed, the specific surface area is about 699 $m^2/g$, the pore volume is about 2.0 $cm^3/g$, and the average pore diameter is 13.8 nm. Therefore, the pore volume after wrapping is slightly decreased. Together with FIG. 4, it is caused by wrapping DsRed in the substrate.

Figure 4:
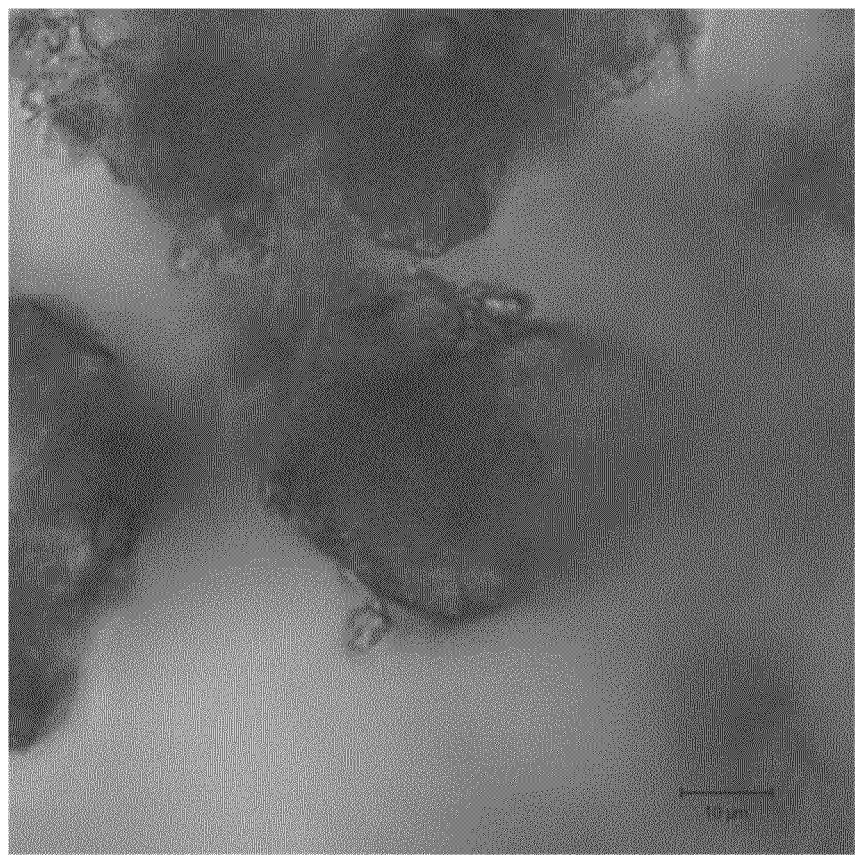
FIG. 4 shows the confocal microscopic image of silica aerogel wrapping DsRed.

3. Test by Confocal Laser Scanning Microscopy (CLSM):

FIG. 4 shows the confocal microscopic image of silica aerogel wrapping DsRed. In general, from a confocal laser scanning microscope, the images of the sample with different depths can be obtained. The information of these images shows dispersion and embedding conditions of DsRed. As shown in FIG. 4, the portion with the dot distribution is DsRed. FIG. 4 shows that DsRed is well wrapped and evenly dispersed. The bio-composite is successfully fabricated. It is an important breakthrough for the application of silica aerogel.

Figure 5:
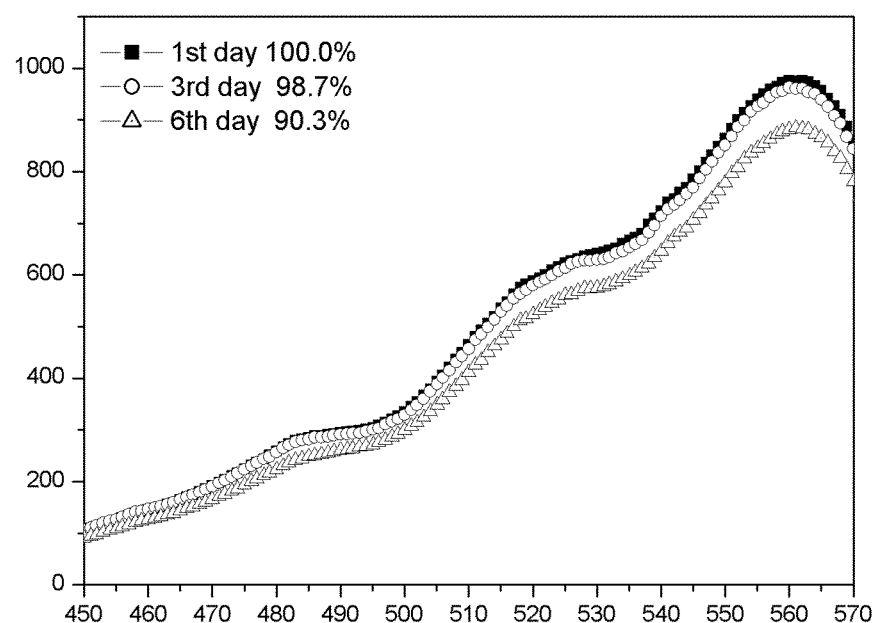
FIG. 5 shows the photoluminescent spectrum of DsRed at a room temperature and excited by a light source with a wavelength of 558 nm.
Figure 6:
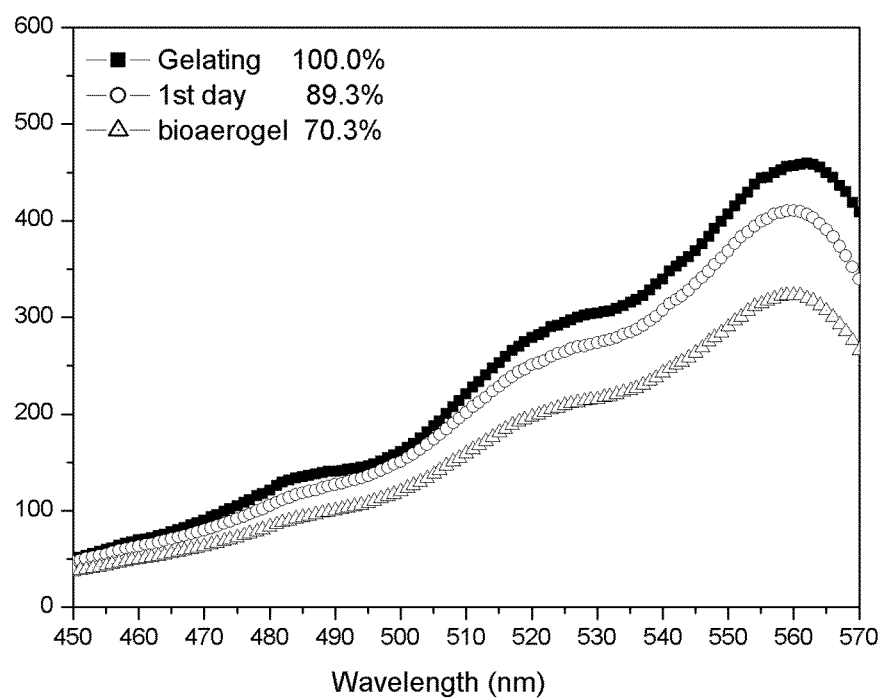
FIG. 6 shows the photoluminescent spectrum of silica aerogel wrapping DsRed at a room temperature and excited by a light source with a wavelength of 558 nm.

4. Test by a Fluorescence Spectrophotometer:

FIGS. 5 and 6 show the photoluminescent spectra of DsRed and biograde aerogel at a room temperature and excited by a light source with a wavelength of 558 nm. In principle, the aerogel doped with DsRed is tested by 558 nm excitation light and 583 nm absorption light. The aerogel doped with EGFP is tested by 488 nm excitation light and 507 nm absorption light. The survival rate is detected with a percentage. FIG. 5 shows three characteristic peaks of DsRed and the activity slightly decreases with time. FIG. 6 shows the activity detection of the silica aerogel after wrapping DsRed. It is found that on the first day after wrapping the activity decreases by a higher degree, about 11%. After that, the skeleton of the silica aerogel is gradually formed to wrap and protect DsRed. Therefore, the activity appears to be a relative stable value. The activity is still high and more than 70%, even through removing the template. It provides an excellent development platform for future applications.

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A method for fabricating biocomposite, comprising:
providing a precursor solution, wherein said precursor solution comprises:
a hydrophilic ionic liquid, wherein the hydrophilic ionic liquid is formed by mixing an organic base with a Lewis acid wherein the Lewis acid is not halogenated metal acid, wherein a cationic moiety in said organic base is alkyl or aryl group having the following general equation,

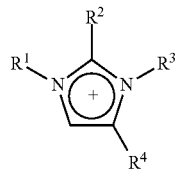

wherein $R^1$, $R^2$, $R^3$, and $R^4$ are selected according to the following table,

| $R^1$ | $R^2$ | $R^3$ | $R^4$ |
|---|---|---|---|
| $CH_3$ | H | $CH_3$ | H |
| $C_2H_5$ | H | $C_2H_5$ | H |
| $CH_3CH_2CH_2CH_2$ | H | $CH_3$ | H |
| $(CH_3)_2CHCH_2$ | H | $CH_3$ | H |
| $CH_3CH_2CH_2CH_2$ | H | $C_2H_5$ | H |
| $CH_3$ | H | $CH_3OCH_2CH_2$ | H |
| $CH_3$ | H | $CF_3CH_2$ | H |
| $CH_3$ | $CH_3$ | $C_2H_5$ | H |
| $CH_3$ | $CH_3$ | $CH_3CH_2CH_2$ | H |
| $C_6H_6CH_2$ | $CH_3$ | $CH_3CH_2CH_2$ | H |
| $C_6H_6CH_2$ | $CH_3$ | $CH_3CH_2CH_2CH_2$ | H |
| $C_6H_6CH_2$ | $CH_3$ | $(CH_3CH_2)(CH_3)CH$ | H |
| $C_6H_6CH_2$ | $CH_3$ | $CH_3CH_2CH_2CH_2$ | H |
| $CH_3$ | H | $C_2H_5$ | $CH_3$ |
| $C_2H_5$ | H | $C_2H_5$ | $CH_3$; | a catalyst comprising one selected from the group consisting of alcohol, buffer, and a combination thereof;
at least one biomolecule; and
at least one alkoxide monomer and/or aryloxide monomer;
curing the precursor solution by hydrolyzing and polymerizing said at least one alkoxide monomer and/or aryloxide monomer in the precursor solution to form an aerogel wrapping said at least one biomolecule to form said biocomposite; and
extracting hydrophilic ionic liquid from the biocomposite by substituting a solvent for the hydrophilic ionic liquid.

2. The method according to claim 1, wherein an anionic moiety in said Lewis acid comprises one selected from the group consisting of the following: $BF_4{-}$, $PF_6{-}$, $AsF_6{-}$, $SbF_6{-}$, $F(HF)_n{-}$, $CF_3SO_3{-}$, $CF_3CF_2CF_2CF_2SO_3{-}$, $(CF_3SO_2)_2N{-}$, $(CF_3SO_2)_3C{-}$, $CF_3COO{-}$, and $CF_3CF_2CF_2COO{-}$.

3. The method according to claim 1, wherein said biomolecule comprises one selected from the group consisting of the following: antigens, monoclonal antibodies, polyclonal antibodies, nucleic acids comprising monomeric and oligomeric types, proteins, enzymes, lipids, polysaccharides, sugars, peptides, polypeptides, drugs, viruses, microbes, and bioligands.

4. The method according to claim 1, wherein said alkoxide monomer and/or aryloxide monomer comprises an element selected from the group consisting of the following: Li, Na, K, Rb, Cs, Be, Mg, Ca, Sr, Ba, Ti, Te, Cr, Cu, Er, Fe, Ta, V, Zn, Zr, Al, Si, Ge, Sn, and Pb.

5. The method according to claim 1, wherein said alkoxide monomer and/or aryloxide monomer comprises one selected from the group consisting of the following: tetramethyl orthosilicate (TMOS), tetraethoxy orthosilicate (TEOS), bis (triethoxysilyl) ethane (BTSE), bis(triethoxysilyl)benzene (BTSB), tetrabutyl titanate (TBOT), and vanadium oxytriproposide.

6. The method according to claim 1, wherein said hydrophilic ionic liquid is room temperature ionic liquid (RTIL).

7. The method according to claim 1, wherein the weight of said hydrophilic ionic liquid is about 10%~90% of the precursor solution.

8. The method according to claim 1, wherein the weight of said hydrophilic ionic liquid is about 20%~50% of the precursor solution.

9. The method according to claim 1, wherein said buffer has a pH value about 5~9.

10. The method according to claim 1, wherein said curing process comprises:
hydrolyzing and polymerizing said at least one alkoxide monomer and/or aryloxide monomer until said precursor solution has a specific viscosity more than 150 cps; and
continuing hydrolyzing and polymerizing said at least one alkoxide monomer and/or aryloxide monomer to form said aerogel.

11. The method according to claim 10, wherein said specific viscosity is more than or equal to 200 cps.

12. The method according to claim 1, wherein said curing process is carried out at a temperature less than or equal to 50° C.

13. The method according to claim 1, wherein said solvent comprises one selected from the group consisting of the following: alcohol, water, and buffer solution.

14. The method according to claim 13, wherein said buffer solution has a pH value about 5~9.

15. The method according to claim 1, wherein said extracting is carried out at a temperature less than or equal to 50° C.

16. The method according to claim 1, further comprising drying the biocomposite to remove said solvent substituted for the hydrophilic ionic liquid.

17. The method according to claim 16, wherein said drying is carried out at a temperature less than or equal to 0° C.

18. The method according to claim 16, wherein said drying is carried out at a pressure less than or equal to 20 Pa.

19. The method according to claim 1, wherein said biocomposite contains specific surface area more than or equal to 100 $m^2/g$.

20. The method according to claim 1, wherein said biocomposite contains an average diameter ranging about 1 nm to 50 nm.

21. The method according to claim 1, wherein said biocomposite has porosity ranging about 50% to 99%.

22. The method according to claim 1, wherein said biocomposite contains pore volume more than or equal to 1.0 $cm^3/g$.

* * * * *